United States Patent
Mehta et al.

(10) Patent No.: US 6,982,349 B1
(45) Date of Patent: Jan. 3, 2006

(54) PROCESS FOR PRODUCING ATENOLOL OF HIGH OPTICAL PURITY

(75) Inventors: Satish Ramanlal Mehta, Maharashtra (IN); Baburao Manikroa Bhawal, Maharashtra (IN); Vishnu Hari Deshpande, Maharashtra (IN); Mukund Keshav Gurjar, Maharashtra (IN)

(73) Assignee: Emcure Pharmaceuticals Limited, Pune (IN)

( * ) Notice: Subject to any disclaimer, the term of this patent is extended or adjusted under 35 U.S.C. 154(b) by 0 days.

(21) Appl. No.: 10/701,942

(22) Filed: Nov. 5, 2003

(30) Foreign Application Priority Data

Oct. 31, 2003 (IN) ............... 1148/MUM/2003

(51) Int. Cl.
*C07C 233/05* (2006.01)
(52) U.S. Cl. ............ 564/165; 549/514; 549/515; 549/516
(58) Field of Classification Search ............ 564/165; 549/514–516
See application file for complete search history.

(56) References Cited

U.S. PATENT DOCUMENTS 4,085,136 A 4/1978 Tucker 5,223,646 A 6/1993 Takehira et al.

FOREIGN PATENT DOCUMENTS

| JP | 01-102072 | * | 4/1989 |
| JP | 3077856 |   | 3/1991 |
| JP | 04-198175 | * | 7/1992 |

OTHER PUBLICATIONS

Kitaori, Kazuhiro, (1997) Chem. Pharm. Bull 45(2) 412-414.
Wilson, Michael, (1988) J. Chromatography (431) pp. 222-227.

* cited by examiner

*Primary Examiner*—Shailendra Kumar
(74) *Attorney, Agent, or Firm*—John P. White, Esq.; Cooper & Dunham LLP

(57) ABSTRACT

The present invention relates to an improved process for producing optically active (S)-atenolol of formula (1) in high optical purity by reacting a phenol with an epichlorohydrin.

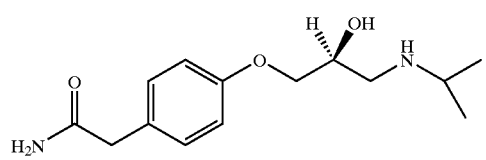

8 Claims, No Drawings

PROCESS FOR PRODUCING ATENOLOL OF HIGH OPTICAL PURITY

TECHNICAL FIELD

This invention relates to an improved process for producing optically active (S)-atenolol of formula (1) in high optical purity.

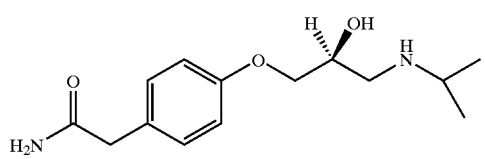

1

PRIOR ART

The compound (R,S)-atenolol (4-[2-hydroxy-3-[(1-methylethyl)amino]propoxy] -benzeneacetamide) is useful as a β-adrenegic blocker for the treatment of angina pectoris, arrhythmia and hypertension. It is known that atenolol is a 1-aryloxy-3-aminopropane-2-ol derivative wherein the hydroxy bearing carbon is an asymmetric carbon and hence exists as R- and S-isomers. It is also known that the S-isomer is particularly useful as a β-adrenegic blocker in view of its superior pharmacological activities. It is reported that S-atenolol has hypotensive activity and activity on brachycardia (A. A. Pearson, T. E. Gaffney, T. Walle, P. J. Privitera; *J. Pharmacol. Exp. Ther.*, 250(3), 759, 1989).

In prior art, the optical resolution of racemic atenolol has been studied to obtain the desired optically active atenolol, however, any practical method has not been reported so far. It is also reported that the diastereomers of atenolol having high purity is obtained from racemic mixture by using (R,R)-O,O-di-toluoyltartaric acid anhydride (M. J. Wilson et al., *J. Chromatogr.* (NLD) 431 (1), 222–227, 1988). However, this method is not suitable for large scale production of optically active atenolol as it requires a large volume of solvent and further it is technically very troublesome to recycle (R,R)-O,O-di-toluoyltartaric acid anhydride.

Another method of preparing optically active atenolol has been proposed in JP-A-50-77331 and DE-A-2453324:

Wherein Z is halogen atom or sulphonyloxy group, and * means asymmetric carbon.

However, this process has some disadvantages as this process requires several steps for obtaining optically active S-atenolol stating from D-manitol; moreover the yield of S-atenolol by this process is less than 50% and the optical purity is just about 80% ee.

Another method for the preparation of S-atenolol has been reported in U.S. Pat. No. 5,223,646 which consists of reacting sodium salt of 4-carbamoylmethylphenol with R-epichlorohydrin at 0° to 35° C. to obtain an intermediate—an optically active glycidyl ether and then reacting the optically active intermediate glycidyl ether with isopropylamine to obtain S-atenolol (see also EP-435068 A2; EP-605384; JP 03077856 A2). It has also been reported that the above procedure gives optically active glycidyl ether and atenolol of 90–96% ee optical purity. According to this report, the optical purity of atenolol may be enhanced to 98% or higher, if the intermediate optically active glycidyl ether is repeatedly recrystallised from a suitable solvent. It has also been reported that the optically active atenolol in an optical purity of 98% or higher can be produced from atenolol of lower optical purity by converting it to its salt with Bronsted's acid (K. Kazuhiro; T. Yosikazu; F. Yoshiro; Y. Hiroshi; O. Junzo, *Chem. Pharm. Bull.*, 46(3), 505–507, 1998).

The separation of the atenolol salt having higher optical purity (>98% ee) is carried out by dissolving the atenolol salt having lower optical purity in a solvent, precipitating solid materials having a high content of racemic atenolol salt, and then isolating the desired atenolol salt having higher optical purity (>98% ee) by solid-liquid separation method. The optically active salt having high optical purity is then subjected to removal of acid moiety to isolate the desired optically active atenolol in free form. Though this process yields atenolol of higher optical purity, it involves salt formation and tedious separation of racemic salt from an optically active salt, which leads to the lower yields of desired optically active atenolol. Further, the salt has to be converted to free atenolol either by neutralisation or using ion exchange resins. Thus, this process gives lower overall yield of the desired optically active atenolol is low.

There is therefore a need to provide a process whereby S-atenolol may be obtained in high yield and high optical purity.

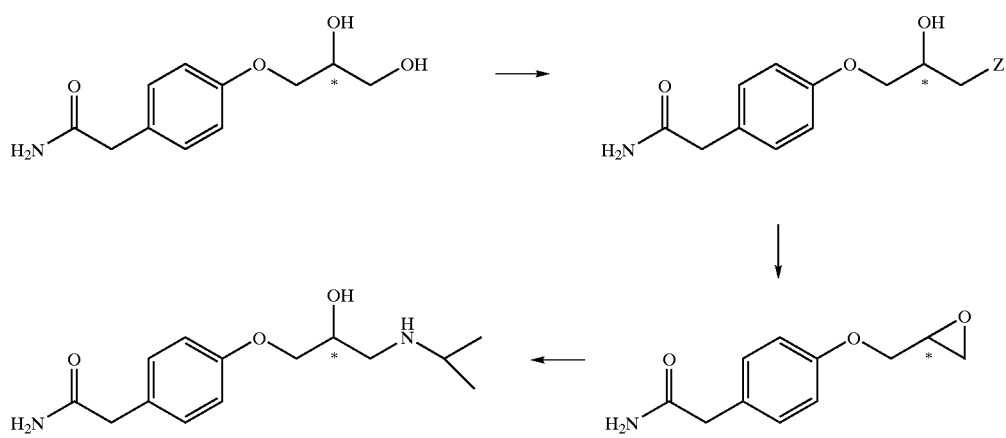

OBJECTS OF THE INVENTION

The main objective of the present invention is to provide an improved process for the preparation of optically active atenolol in high optical purity and good yield.

Another objective of this invention is to provide simple process for optically active atenolol devoid of tedious recrystallization step or salt formation and salt separation steps.

DETAILED DESCRIPTION OF THE INVENTION

Accordingly, the present invention provides a process for the preparation of (S)-atenolol (1), which comprises the steps of:

a) reacting a phenol of formula 2:

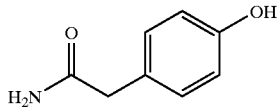

with an (R)-epichlorohydrin of formula (3):

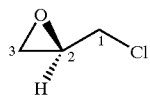

in presence of an alkali metal hydroxide and a quaternary ammonium salt as phase transfer catalyst (PTC) in an aqueous solution at a temperature in a range of −10° C. to 0° C. to obtain optically active intermediate glycidyl ether of formula 4:

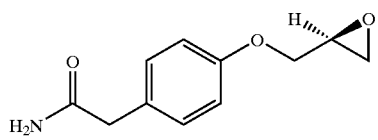

b) reacting the optically active intermediate glycidyl ether (4) with isopropylamine at 10° to 40° C. to obtain (S)-atenolol of the formula 1:

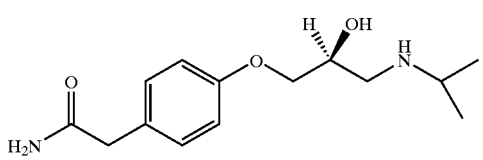

in good chemical yield and high optical purity (>99 ee).

One major advantage of this process is that S-atenolol may be obtained directly without going through the cumbersome step of recrystallization or additional salt formation step, as in the prior art.

The aqueous alkali metal hydroxide used in the process is selected from sodium hydroxide or potassium hydroxide and is used as aqueous solution in 1 to 1.5 moles to 1 mole of the phenol 2. The (R)-epichlorohydrin (3) used in the process is preferably of high optical purity and used in an amount of 1 to 3 moles, more preferably 1 to 1.6 moles, to 1 mole of phenol (2).

The quaternary ammonium salt has the formula:

Wherein $R^1$, $R^2$, $R^3$ and $R^4$ are same or different, each an alkyl group having 1 to 16 carbon atoms (e.g. methyl, ethyl, propyl butyl etc), phenyl or benzyl, X is chlorine, bromine, iodine, hydrogen sulphate or hydroxyl group. The amount of quaternary ammonium salt used is 0.001 to 2% by weight of phenol (2).

The Applicant studied the reaction temperature extensively and found that it plays an important role in deciding optical purity of (S)-atenolol (1) formed via optically active glycidyl ether. When the reaction of phenol (2) and (R)-epichlorohydrin is carried out at 5° C. or at any other higher temperature, (S)-atenolol (1) of a lower optical purity was obtained via optically active glycidyl ether, as for example in EP 435068.

The Applicant, after studying the prior art processes found that during the course of these reactions, the phenoxide (or phenol) attacks the C-1 carbon atom of (R)-epichlorohydrin with the expulsion of chloride to yield (R)-glycidyl ether, which on reaction with isopropyl amine gives (R)-atenolol. The original epoxide ring remains unchanged in the reaction.

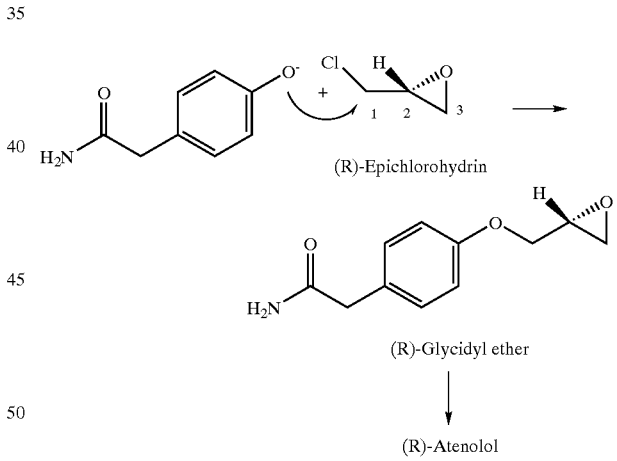

Thus, the reaction of phenol (2) at carbon centre C-1 of (R)-epichlorohydrin by nucleophilic displacement of chlorine leads to the formation of undesired (R)-atenolol via optically active (R)-glycidyl ether as a side product, which accounts for the low yield of optically active S-atenolol in the prior art.

The Applicant then conducted this reaction at a lower temperature and found to their surprise that S-atenolol could be obtained in high yield. The reason is that during the course of reaction, the phenoxide (or phenol) ion attacks the C-3 carbon atom of (R)-epichlorohydrin and opens the epoxide ring. The new epoxide ring formation takes place by the attack of O⁻ on C-3 carbon with expulsion of chloride to give (S)-glycidyl ether, which on reaction with isopropyl amine gives (S)-atenolol. Thus, the reaction of phenol (2) at carbon centre C-3 of (R)-epichlorohydrin leads to the formation desired (S)-atenolol (1) as a major product via optically active glycidyl ether (4).

Both these reactions occurring on different atoms are shown as path 'a' and path 'b' in the following scheme herebelow.

Path 'a' is the process of the present invention whereas path 'b' is the process of the prior art.

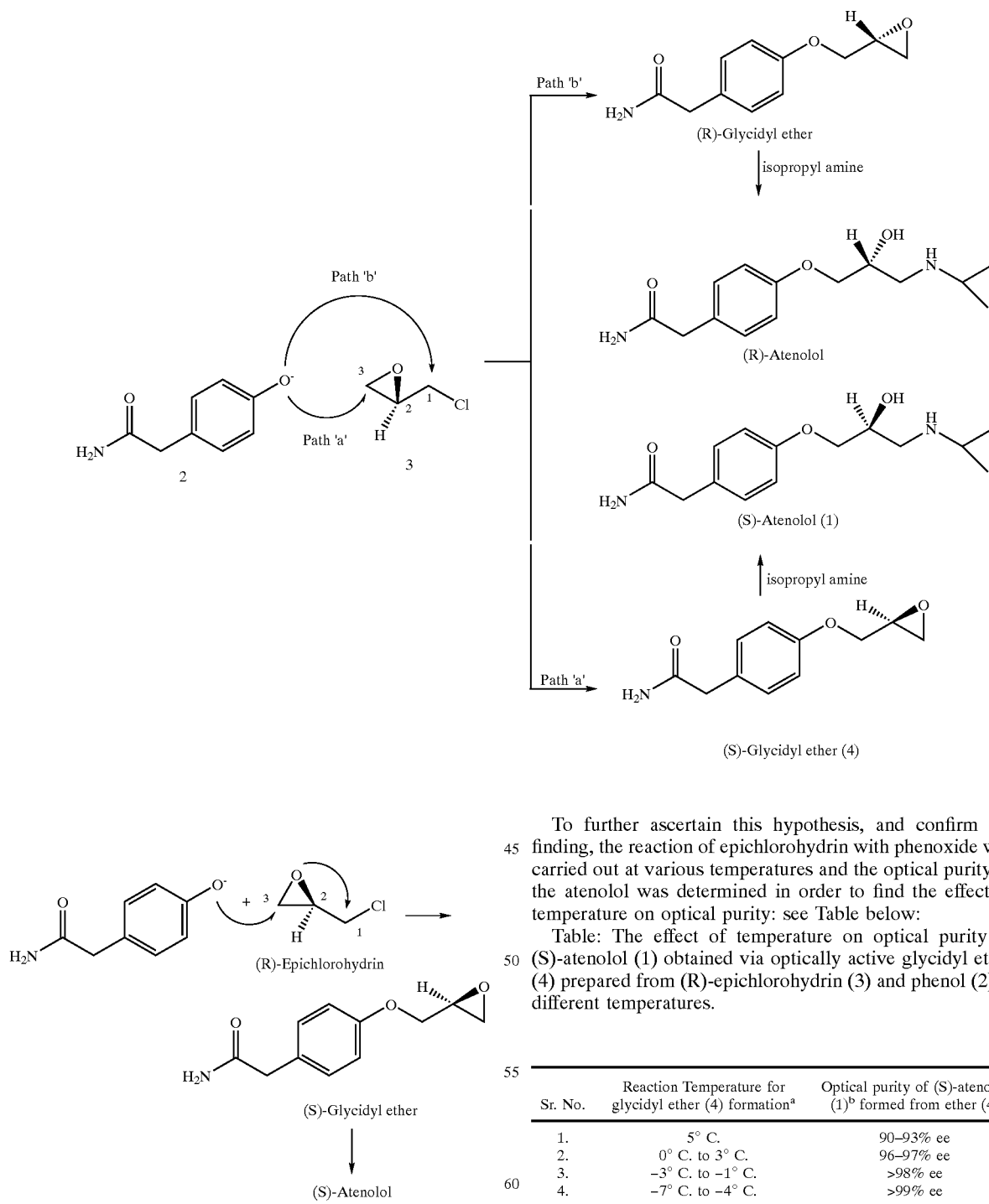

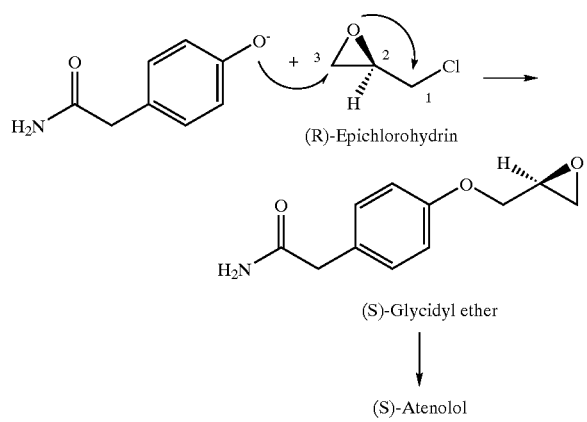

The lower optical purity in (S)-atenolol formation in the prior art may therefore be on account of the slow reaction rate at carbon atom 1 and the high yield of S-atenolol obtained by the process of the present invention may be due to the reaction at carbon atom 3 of (R)-epichlorohydrin (3).

To further ascertain this hypothesis, and confirm the finding, the reaction of epichlorohydrin with phenoxide was carried out at various temperatures and the optical purity of the atenolol was determined in order to find the effect of temperature on optical purity: see Table below:

Table: The effect of temperature on optical purity of (S)-atenolol (1) obtained via optically active glycidyl ether (4) prepared from (R)-epichlorohydrin (3) and phenol (2) at different temperatures.

| Sr. No. | Reaction Temperature for glycidyl ether (4) formation[a] | Optical purity of (S)-atenolol (1)[b] formed from ether (4) |
| --- | --- | --- |
| 1. | 5° C. | 90–93% ee |
| 2. | 0° C. to 3° C. | 96–97% ee |
| 3. | −3° C. to −1° C. | >98% ee |
| 4. | −7° C. to −4° C. | >99% ee |

[a]All reactions were carried out at specified temperature for 50–60 hrs.
[b](S)-atenolol is obtained from optical active glycidyl ether by the reaction of isopropyl amine.

As can be seen from the above table, when the reaction proceeds at 5° C., the yield of S-atenolol is about 90–93% ee whereas, as the temperature is decreased, the yield increases. The S-atenolol is obtained in yield of more than 99% ee when the reaction is effected at −7 to −4° C.

It is to be noted that lowering the temperature and obtaining a choral compound in high optical purity is not a matter of routine optimization by a skilled person. This was a surprising finding that the Applicant found during their routine studies. Only after a detailed investigation, and after much trial and error, and performing several experiments, the Applicant arrived at the conclusion that lowering the temperature would yield a chiral compound in high optical purity.

Accordingly, the reaction of present invention is carried out in the temperature range of −10° C. to +5° C., preferably −7° C. to 0° C. A substantial improvement in the optical purity of intermediate glycidyl ether as well as (S)-atenolol (1) obtained from this optically active intermediate glycidyl ether was observed when the glycidyl ether formation reaction is carried out at −7 to 0° C. for 50 hrs followed by the reaction of this glycidyl.

Accordingly, the reaction of present invention is carried out in the temperature range of −10° C. to +5° C., preferably −7° C. to 0° C. A substantial improvement in the optical purity of intermediate glycidyl ether as well as (S)-atenolol (1) obtained from this optically active intermediate glycidyl ether was observed when the glycidyl ether formation reaction is carried out at −7 to 0° C. for 50 hrs followed by the reaction of this glycidyl ether with isopropyl amine, which produced directly (S)-atenolol (1) of high optical purity (99% ee), which could be isolated after removal of excess isopropyl amine followed by simple work up procedure.

In an embodiment, a side reaction product, optically active chlorohydrin of formula 5:

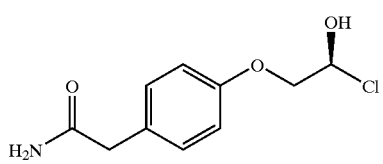

5 is formed in a varying amounts. However, this optically active chlorohydrine (5) may also be converted into the desired (S)-atenolol (1) by reacting it with isopropylamine, and hence, the contamination thereof does not affect the optical purity of (S)-atenolol (1) in the present invention.

The reaction of phenol (2) and (R)-epichlorohydrin is carried out at −7° C. to 0° C. for 45 to 55 hrs. With the progress of the reaction, the optically active glycidyl ether is precipitated; the precipitated solid can be isolated from the reaction mixture by a conventional method such as filtration to obtain optically active glycidyl ether (4) as a solid.

The optically active glycidyl ether (4) obtained by above process may be used in the subsequent reaction with isopropylamine to give (S)-atenolol (1) by known method. Thus, the optically active glycidyl ether (4) (1 mole) is reacted with excess of isopropylamine (5 to 30 mole) in a solvent such as water or a lower alcohol, such as methanol, ethanol, isopropanol etc. or a mixture of water and an alcohol with stirring at 5° to 30° C. for 6 to 24 hrs. The solvent used is 1 to 20 parts by weight to 1 part by weight of the optically active glycidyl ether (4).

In order to prevent the reaction of produced atenolol with the optically active glycidyl ether (4) it is preferable to add the optically active glycidyl ether (4) to isopropyl amine in a solvent. The removal of excess isopropyl amine by distillation gave desired (S)-atenolol (1). Preferably, the distillation is carried out at atmospheric pressure at the initial stages and under reduced pressure at later stages, keeping the reaction mass temperature below 60° to 70° C., through out the distillation process. The crude residue may be purified, if required, by dissolving it in 1N HCl, treating this solution with activated charcoal, filtering the charcoal followed by treatment of alkali to precipitate the product. Thus, the solid product was isolated by conventional method such as filtration to get (S)-atenolol (1) of optical purity of 98% ee and above. If, necessary, the optically active (S)-atenolol (1) may be crystallized from an appropriate solvent such as water, alcohols, such as methanol, ethanol, isopropyl alcohol, butanol etc., ethers, such as diethyl ether, methyl tbutyl ether, diisopropyl ether or ketones, such as acetone, ethyl methyl ketone, methyl isobutyl ketone etc.

The process of the present invention is described herein below with reference to examples, which are illustrative only and should not be construed to limit the scope of the present invention in any manner.

The optical purity (enantiomeric excess, ee) is determined by Chiral HPLC using Chiracel-OD column.

EXAMPLE 1

A mixture of (R)-epichlorohydrin ($[\alpha]_D^{25}$: −35.1 (neat), 138.75 g, 1.5 mole) and water (82 ml) was cooled to −7° C. and to this cold reaction mixture is added a solution of 4-hydroxyphenyl acetamide of formula 1 (151.00 g, 1 mole) and benzyltrimethylammonium chloride (1.3 g) in sodium hydroxide [40 g, 1 mole; dissolved in water (670 ml)] with stirring over a period of 3 hrs. maintaining the temperature at −7° C. to −5° C. The reaction mixture is then stirred further at −7° C. to −5° C. for 50 hrs. The precipitated solid is filtered, washed with water and dried at 60° C. to give 176 g of a mixture of S-glycidyl ether of formula 4 and S-chlorohydrin of formula 5 in about 3:2 ratio. m.p. 159–161° C.

EXAMPLE 2

A mixture of isopropylamine (1.1 kg) and water (200 ml) is cooled to 10° C. and a mixture of S-glycidyl ether of formula 4 and S-chlorohydrin of formula 5 obtained in Example 1 (176 g) is added to it in lots maintaining temperature between 10 to 15° C. over a period of 3 hrs. The reaction is then stirred further for another 10 hr. The excess of isopropylamine is removed by distillation and the residue was treated with the water. The slurry so obtained is acidified with 5N HCl to pH 2.0. The resulting solution is then filtered, washed with water. The filtrate is basified with 2N NaOH to pH 11.7 and precipitated solid is filtered washed with water and dried to get (S)-atenolol (206 g, 91%) in 99.1% ee when analysed by using Chiracel OD column.

m.p. 152–153° C.

$[\alpha]_D^{25}$: −17.2 (c=1.0, 1N HCl).

IR: $\nu_{max}$ 3352, 3168, 1635, 1242 cm$^{-1}$.

$^1$H NMR (DMSO-d$_6$): δ 0.99 (d, J=7 Hz, 6H, 2×CH$_3$), 2.60 (m, 1H, CH), 2.74 (m, 2H, CH$_2$), 3.27 (s, 2H, CH$_2$), 3.88 (m, 4H, CH$_2$, CH, NH), 6.83 (d, J=8 Hz, 2H, Ar—H), 7.14 (d, J=8 Hz, 2H, Ar—H), 7.40 (bs, 1H). $^{13}$C NMR (DMSO-d$_6$): 22.01, 22.09, 41.26, 48.39, 49.38, 67.73, 70.58, 114.16, 128.41, 129.93, 157.17, 172.59 ppm.

EXAMPLE 3

A mixture of (R)-epichlorohydrin (148.00 g, 1.6 mole) and water (90 ml) is cooled to 0° C. and to this cold reaction mixture is added a solution of 4-hydroxyphenyl acetamide of formula 1 (151.00 g, 1 mole) and benzyltrimethylammonium chloride (1.8 g) in sodium hydroxide [40 g, 1 mole; dissolved in water (670 ml)] with stirring over a period of 4 hrs. maintaining the temperature at 0° C. to 3° C. The reaction mixture is then stirred further at 0° C. to 3° C. for 45 hrs. The precipitated solid was filtered, washed with water and dried to give 185 g of a mixture of S-glycidyl ether of formula 4 and S-chlorohydrin of formula 5 in about 7:3 ratio. m.p. 153–154° C.

EXAMPLE 4

A mixture of isopropylamine (1.2 kg) and water (200 ml) is cooled to 10° C. and a mixture of S-glycidyl ether of formula 4 and S-chlorohydrin of formula 5 obtained in Example 3 (185 g) is added to it in lots maintaining temperature between 10 to 15° C. over a period of 3 hrs. The reaction is then stirred further for another 10 hr. The excess of isopropylamine is removed by distillation and the residue was treated with the water. The slurry so obtained is acidified with 5N HCl to pH 1.5. The resulting solution is then filtered, washed with water. The filtrate is basified with 2N NaOH to pH 12.0 and precipitated solid is filtered washed with water and dried to get (S)-atenolol (215 g, 90%) in 96.8% ee when analysed by using Chiracel OD column.

m.p. 151–152° C.

$[\alpha]_D^{25}$: −16.1 (c=1.0, 1N HCl).

EXAMPLE 5

A mixture of (R)-epichlorohydrin (111.00 g, 1.2 mole) and water (70 ml) is cooled to 0° C. and to this cold reaction mixture is added a solution of 4-hydroxyphenyl acetamide of formula 1 (151.00 g, 1 mole) and benzyltriethylammonium chloride (1.5 g) in sodium hydroxide [40 g, 1 mole; dissolved in water (700 ml)] with stirring over a period of 6 hrs. maintaining the temperature at 0° C. to 3° C. The reaction mixture is then stirred further at 0° C. to 3° C. for 42 hrs. The precipitated solid is filtered, washed with water and dried to give 149.2 g of a mixture of S-glycidyl ether of formula 4 and S-chlorohydrin of formula 5 in about 7:3 ratio. m.p. 161–162° C.

EXAMPLE 6

A mixture of isopropylamine (850 g) and water (300 ml) is cooled to 10° C. and a mixture of S-glycidyl ether of formula 4 and S-chlorohydrin of formula 5 obtained in Example 5, (149.2 g) is added to it in lots maintaining temperature between 10 to 15° C. over a period of 3 hrs. The reaction is then stirred further for another 12 hr. The excess of isopropylamine is removed by distillation and the residue was treated with the water. The slurry so obtained is acidified with 5N HCl to pH. 1.5. The resulting solution is then filtered, washed with water. The filtrate is basified with 2N NaOH to pH 12.0 and precipitated solid is filtered washed with water and dried to get (S)-atenolol (154.5 g, 80%) in 96.1% ee when analysed by using Chiracel OD column.

m.p. 152–153° C.

$[\alpha]_D^{25}$: −15.9 (c=1.0, 1N HCl).

EXAMPLE 7

A mixture of (R)-epichlorohydrin (120.25 g, 1.3 mole) and water (80 ml) is cooled to −7° C. and to this cold reaction mixture is added a solution of 4-hydroxyphenyl acetamide of formula 1 (151.00 g, 1 mole) and tetrabutylammonium bromide (1.0 g) in sodium hydroxide [40 g, 1 mole; dissolved in water (670 ml)] with stirring over a period of 3 hrs. maintaining the temperature at −7° C. to −5° C. The reaction mixture is then stirred further at −7° C. to −5° C. for 50 hrs. The precipitated solid was filtered, washed with water and dried at 60° C. to give 168 g of a mixture of S-glycidyl ether of formula 4 and S-chlorohydrin of formula 5 in about 5:3 ratio. m.p. 157–159° C.

EXAMPLE 8

A mixture of isopropylamine (1.0 kg) and water (200 ml) is cooled to 10° C. and a mixture of S-glycidyl ether of formula 4 and S-chlorohydrin of formula 5 obtained in Example 7 (168 g) is added to it in lots maintaining temperature between 10 to 15° C. over a period of 3 hrs. The reaction is then stirred further for another 10 hr. The excess of isopropylamine is removed by distillation and the residue was treated with the water. The slurry so obtained is acidified with 5N HCl to pH 2.0. The resulting solution is then filtered, washed with water. The filtrate is basified with 2N NaOH to pH 11.7 and precipitated solid is filtered washed with water and dried to get (S)-atenolol (184 g, 85%) in 99.0% ee when analysed by using Chiracel OD column.

m.p. 152–153° C.

$[\alpha]_D^{25}$: −17.1 (c=1.0, 1N HCl).

EXAMPLE 9

A mixture of (R)-epichlorohydrin (138.75 g, 1.5 mole) and water (90 ml) is cooled to 5° C. and to this cold reaction mixture is added a solution of 4-hydroxyphenyl acetamide of formula 1 (151.00 g, 1 mole) and cetyltrimethylammonium chloride (1.4 g) in sodium hydroxide [40 g, 1 mole; dissolved in water (700 ml)] with stirring over a period of 6 hrs. maintaining the temperature at 4° C. to 5° C. The reaction mixture is then stirred further at 4° C. to 5° C. for 40 hrs. The precipitated solid was filtered, washed with water and dried at 60° C. to give 180 g of a mixture of S-glycidyl ether of formula 4 and S-chlorohydrin of formula 54:1 ratio. m.p. 162–163° C.

EXAMPLE 10

A mixture of isopropylamine (1.2 kg) and water (400 ml) is cooled to 10° C. and a mixture of S-glycidyl ether of formula 4 and S-chlorohydrin of formula 5' obtained in Example 9 (180 g) is added to it in lots maintaining temperature between 10 to 15° C. over a period of 3 hrs. The reaction is then stirred further for another 12 hr. The excess of isopropylamine is removed by distillation and the residue was treated with the water. The slurry so obtained is acidified with 5N HCl to pH 1.8. The resulting solution is then filtered, washed with water. The filtrate is basified with 2N NaOH to pH 12.5 and precipitated solid is filtered washed with water and dried to get (S)-atenolol (181 g, 78%) in 92.0% ee when analysed by using Chiracel OD column.

m.p. 151–152° C.

$[\alpha]_D^{25}$: −15.2 (c=1.0, 1N HCl).

EXAMPLE 11

A mixture of (R)-epichlorohydrin (111.0 g, 1.5 mole) and water (65 ml) is cooled to −3° C. and to this cold reaction mixture is added a solution of 4-hydroxyphenyl acetamide of formula 1 (120.88 g, 0.8 mole) and benzyltrimethylammonium chloride (0.90 g) in sodium hydroxide [32 g, 0.8 mole; dissolved in water (540 ml)] with stirring over a period of 4 hrs. 30 min. maintaining the temperature at −3° C. to 0° C. The reaction mixture is then stirred further at −3° C. to 0° C. for 46 hrs. The precipitated solid was filtered, washed with water and dried at 60° C. to give 145 g of a mixture of S-glycidyl ether of formula 4 and S-chlorohydrin of formula 5 in about 2:1 ratio. m.p. 157–159° C.

EXAMPLE 12

A mixture of isopropylamine (0.950 kg) and water (900 ml) is cooled to 10° C. and a mixture of S-glycidyl ether of formula 4 and S-chlorohydrin of formula 5 obtained in Example 7 (145 g) is added to it in lots maintaining temperature between 10 to 15° C. over a period of 5 hrs. The reaction is then stirred further for another 12 hr. The excess of isopropylamine was removed by distillation and the residue is treated with the water. The slurry so obtained is acidified with 5N HCl to pH 1.5. The resulting solution is then filtered, washed with water. The filtrate is basified with 2N NaOH to pH 12.1 and precipitated solid is filtered washed with water and dried to get (S)-atenolol (140 g, 75%) in 98.2% ee when analysed by using Chiracel OD column.

m.p. 152–153° C.

$[\alpha]_D^{25}$: −16.7 (c=1.0, 1N HCl).

What is claimed is:

1. An improved process for the preparation of (S)-atenolol (1), comprising the steps of:
   a) reacting a phenol of formula:

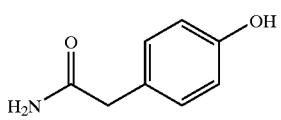
(2)

with an (R)-epichlorohydrin of formula:

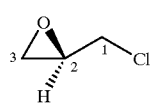
(3)

in the presence of an alkali metal hydroxide and a quaternary ammonium salt as a phase transfer catalyst in a solely aqueous solution at a temperature of −10° C. to 0° C. to obtain optically active intermediate glycidyl ether of formula:

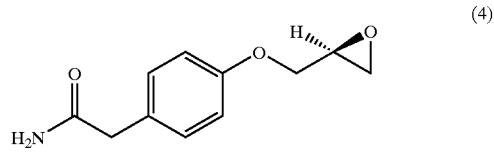
(4)

b) reacting the optically active intermediate glycidil ether (4) with isopropylamine at 10° to 40° C. to obtain (S)-atenolol of formula

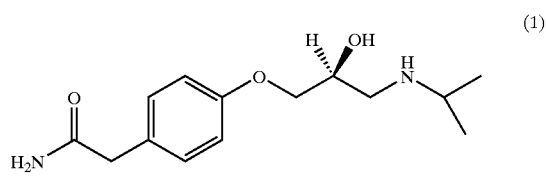
(1)

in high optical purity of >99% ee.

2. The process as claimed in claim 1, wherein the alkali metal hydroxide is selected from sodium hydroxide or potassium hydroxide.

3. The process as claimed in claim 1, wherein the amount of alkali metal hydroxide is 1 to 1.5 moles to 1 mole of the phenol (2).

4. The process as claimed in claim 1, wherein the amount of (R)-epichlorohydrin is 1 to 3 moles to 1 mole of the phenol.

5. The process as claimed in claim 1, wherein the quaternary ammonium salt has the formula $R^1R^2R^3R^4N^+X^-$ wherein each of $R^1$, $R^2$, $R^3$ and $R^4$ is the same or different and is an alkyl group having 1 to 16 carbon atoms, phenyl or benzyl, X is a group selected from chlorine, bromine, iodine, hydrogen sulphate or hydroxyl.

6. The process as claimed in claim 1, wherein the amount of quaternary ammonium salt is 0.001 to 2% by weight of phenol (2).

7. The process as claimed in claim 1 further comprising formation of chlorohydrin as a side product.

8. The process as claimed in claim 7 further comprising reacting chlorohydrin with isopropylamine at 10 to 40° C. to obtain S-atenolol.

* * * * *